US00PP14706P3

(12) United States Plant Patent
Anderson, III et al.

(10) Patent No.: US PP14,706 P3
(45) Date of Patent: Apr. 20, 2004

(54) PISTACHIO ROOTSTOCK NAMED 'P.N. 1-15'

(50) Latin Name: *Pistachio atlantica×integerrima*
Varietal Denomination: P.N. 1-15

(76) Inventors: Henry P. Anderson, III, 1021 E. Cartmill, Tulare, CA (US) 93274; Kenneth L. Puryear, 5911 W. Prospect Dr., Visalia, CA (US) 93291

( * ) Notice: Subject to any disclaimer, the term of this patent is extended or adjusted under 35 U.S.C. 154(b) by 0 days.

(21) Appl. No.: 10/232,050

(22) Filed: Aug. 30, 2002

(65) Prior Publication Data

US 2004/0045060 P1 Mar. 4, 2004

(51) Int. Cl.[7] ..... A01H 5/00
(52) U.S. Cl. ..... Plt./152

(58) Field of Search ..... Plt./152

(56) References Cited

U.S. PATENT DOCUMENTS

PP4,953 P 11/1982 Anderson et al.
PP4,994 P 3/1983 Anderson et al.

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of pistachio tree, characterized by the glossy, medium red to reddish green color of young foliage, the dull, dark green color of mature foliage, and the rounded upright growth habit, which is particularly useful as a rootstock upon which commercial nut bearing pistachio varieties may be budded or grafted.

4 Drawing Sheets

Latin name of genus and species: The present invention relates to a new *Pistachio atlantica×integerrima* tree, designated 'P.N. 1-15'.

BACKGROUND OF THE INVENTION

The present invention relates to a new and distinct variety of pistachio tree, which is a hybrid of *P. atlantica* and *P. integerrima*.

SUMMARY OF THE INVENTION

The 'P.N. 1-15' variety is characterized by the rounded and upright growth of the plant, the glossy, medium red to reddish green color of young foliage, and the dull, dark green color of mature foliage.

The variety is particularly useful as a rootstock upon which commercial nut bearing pistachio varieties may be budded or grafted.

Asexual reproduction by budding onto *P. integerrima* at Kern County, Calif. shows that the foregoing and other distinguishing characteristics come true to form and are established and transmitted through succeeding propagation. Other known forms of asexual reproduction for pistachios may also be employed.

The following is a description of both parents and how they differ from the observed plant of the new variety.

Male Parent: *Pistacia integerrima*. Leaves are pinnately compound with sometimes nine leaflets but usually less. Leaflets are nearly opposite, lanceolate and sessile. Leaflets are significantly larger than the observed plants. Leaflets average 4.35 inches in length and 1.07 inches in width. The entire leaf is about 10.41 inches, including petiole. The petiole is about 0.084 inches in diameter and about 2.82 inches long. Rachis length is about 4.71 inches. The petiole and rachis of the leaf are without reddish coloration. Margins of leaflets are entire with alternate and pinnate venation.

Female Parent: *Pistacia atlantica*. Leaves are pinnately compound with nine leaflets and sometimes less. Leaflets are opposite, lanceolate and sessile. Leaf and leaflets are significantly smaller than observed plant of the new variety. Leaflets average 1.7 inches in length and 0.527 inches in width at the widest point. Entire leaf is about 4.34 inches long including petiole and about 3.31 inches wide. The petiole is about 0.71 inches long and has a diameter of about 0.048 inches. Rachis length is 1.87 inches long. The petiole and rachis are without reddish color. Margins of leaflets are entire with alternate and pinnate venation.

Differences between parents and observed plant of the new variety:

1. Leaf and leaflet size: The male parent's leaves and individual leaflets are considerably larger than those of observed plant of the new variety, while the female parent's leaves and leaflets are considerably smaller.
2. Petiole and rachis: The petiole of the male parent is longer and with larger diameter than the observed plant of the new variety, whereas the petiole of the female parent is smaller than the observed plant. Rachis of male parent is longer than that of the new variety, while the rachis of the female parent is shorter. Both parents are without the reddish petiole and rachis found in the new variety.

BRIEF DESCRIPTION OF ILLUSTRATIONS

The accompanying photographic illustrations show typical specimens of vegetative growth of the new variety, in color as nearly true as it is reasonably possible to make in a color illustration of this character.

Figure 4:
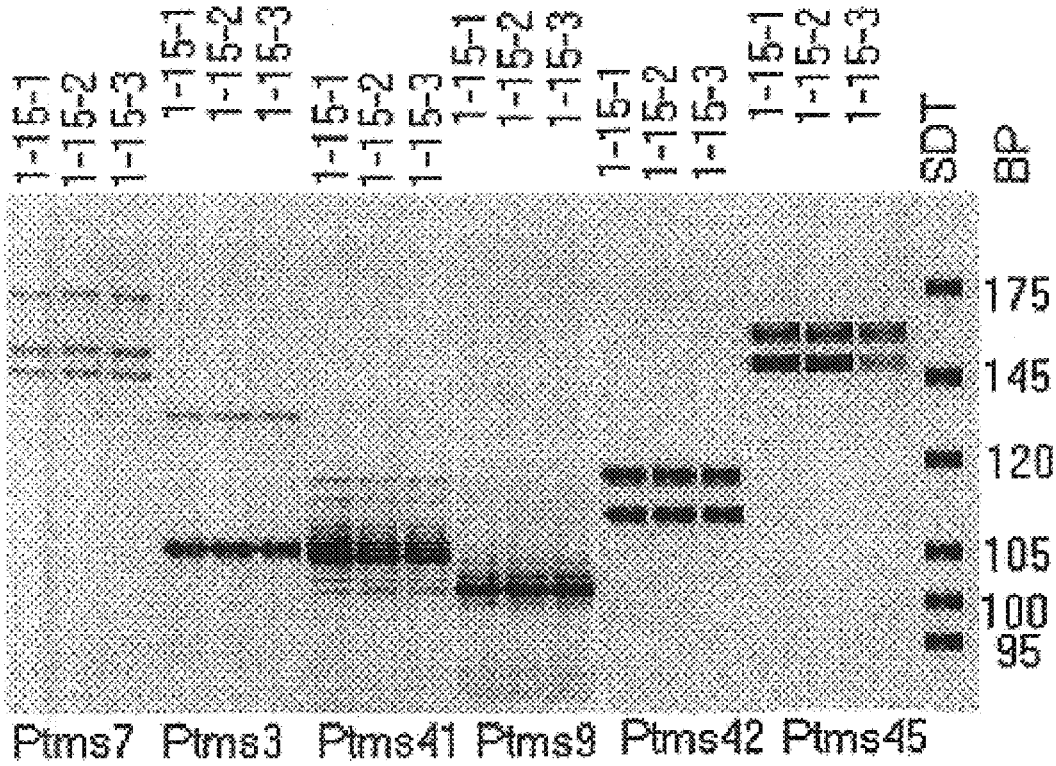

FIG. 4 shows an autoradiogram of a Southern blot, using various microsatellite DNA markers (Ptms7, Ptms3, Ptms41, Ptms9, Ptms42 and Ptms45) as probes directed against DNA isolated from 'P.N. 1-15'. Each marker was run in triplicate. Size markers are shown in the lane labeled "SDT".

DESCRIPTION OF THE NEW VARIETY

Referring now specifically to the new and distinct variety of pistachio tree, the following is a detailed description of one year old trees with color description where indicated by reference to The Royal Horticultural Society Colour Chart, except where common terms of color definition are employed.

The new variety of pistachio tree as herein described may vary in slight detail due to climatic, soil and cultural conditions under which the variety may be grown, the present description being of the variety as grown at McFarland, Kern County, Calif.

Figure 1:
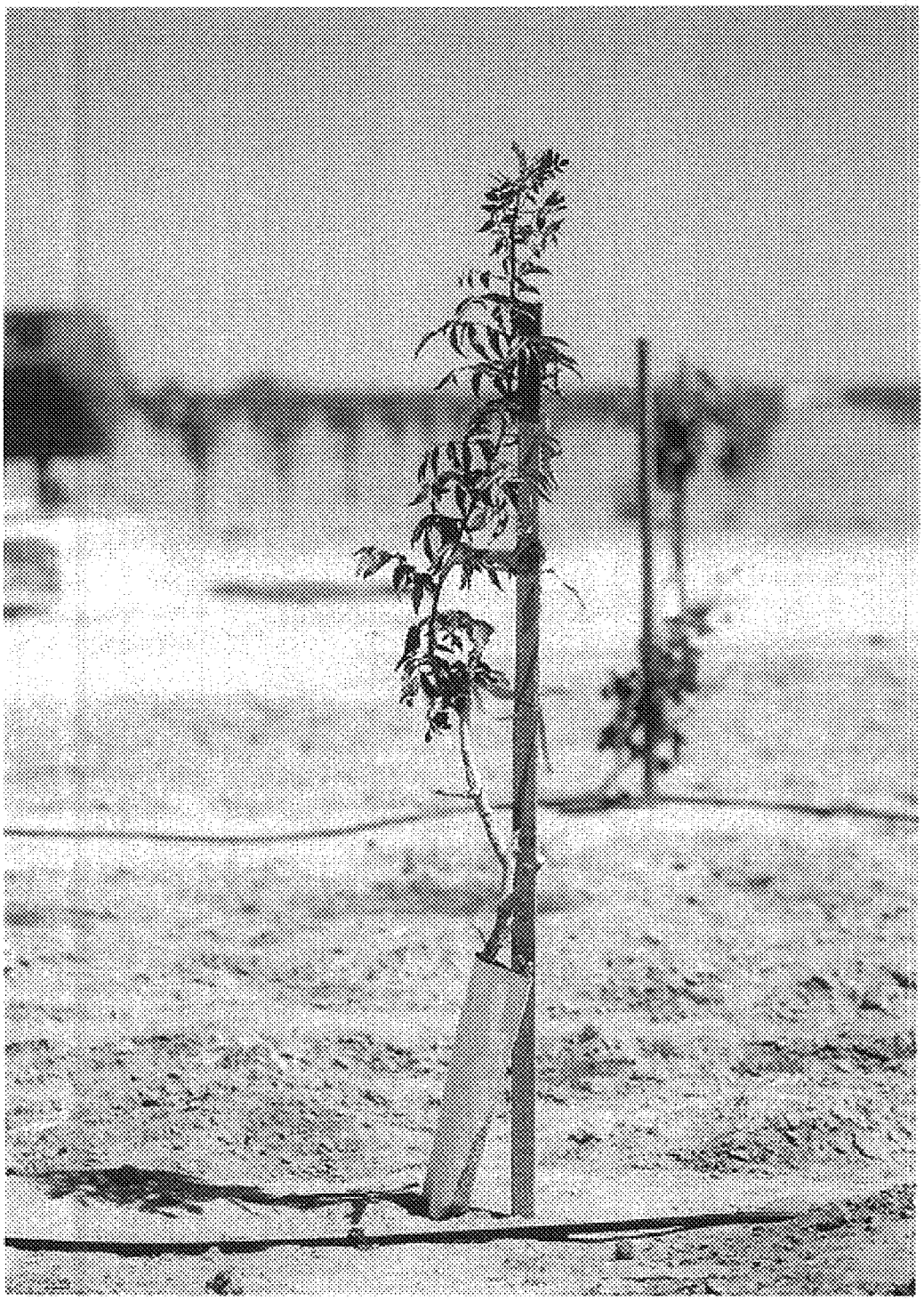
FIG. 1 shows a one year old pistachio tree of the new variety.

Plant:

*Growth.*—Rounded and upright, as indicated in FIG. 1.

Figure 2:
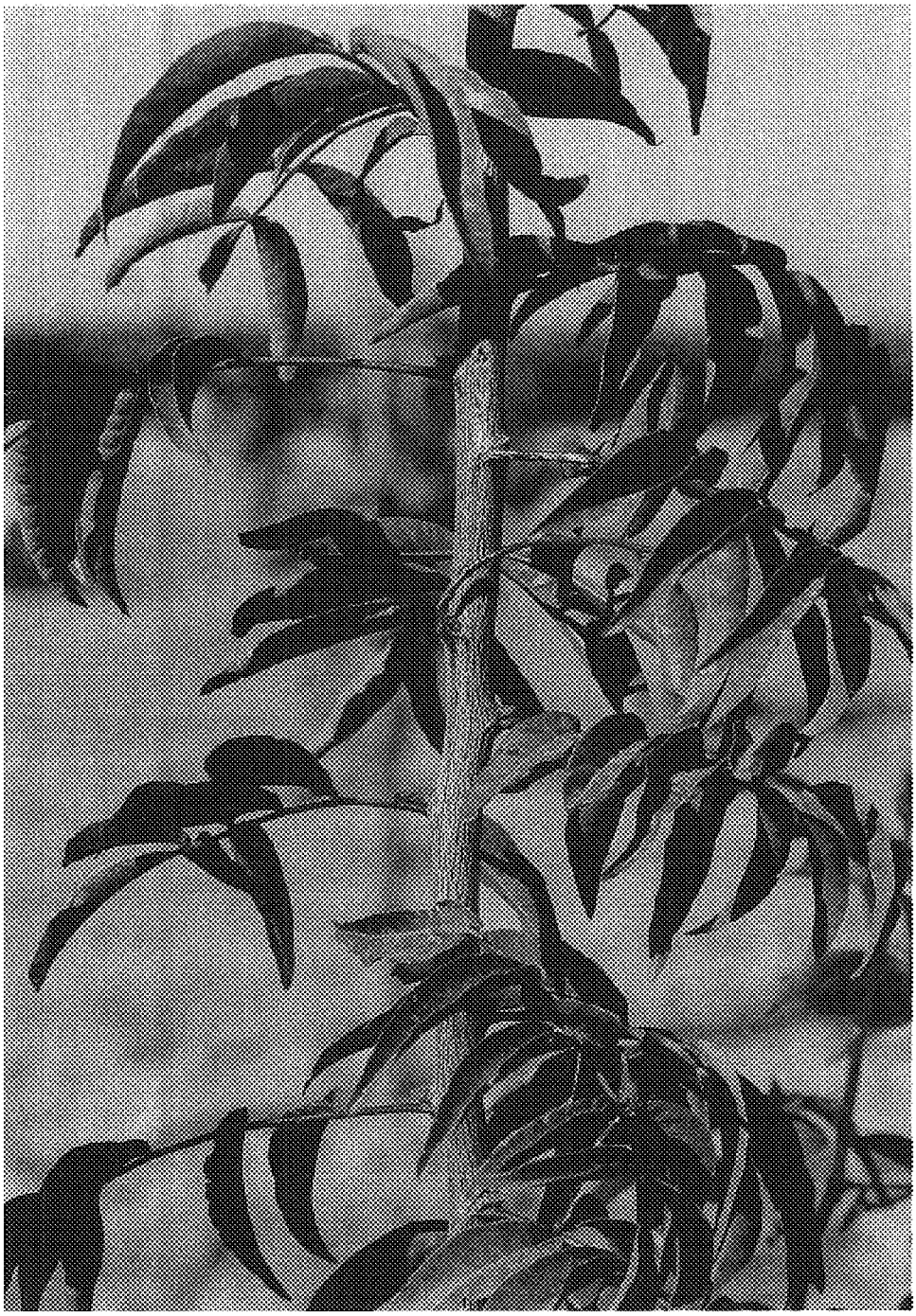
FIG. 2 shows a close-up of the trunk and compound leaves, typically with eleven leaflets.

Foliage:

*Leaves.*—Compound of eleven leaflets (sometimes less), as indicated in FIG. 2. Length and Width — approximately 8.81 inches long and 5.16 inches wide.

Figure 3:
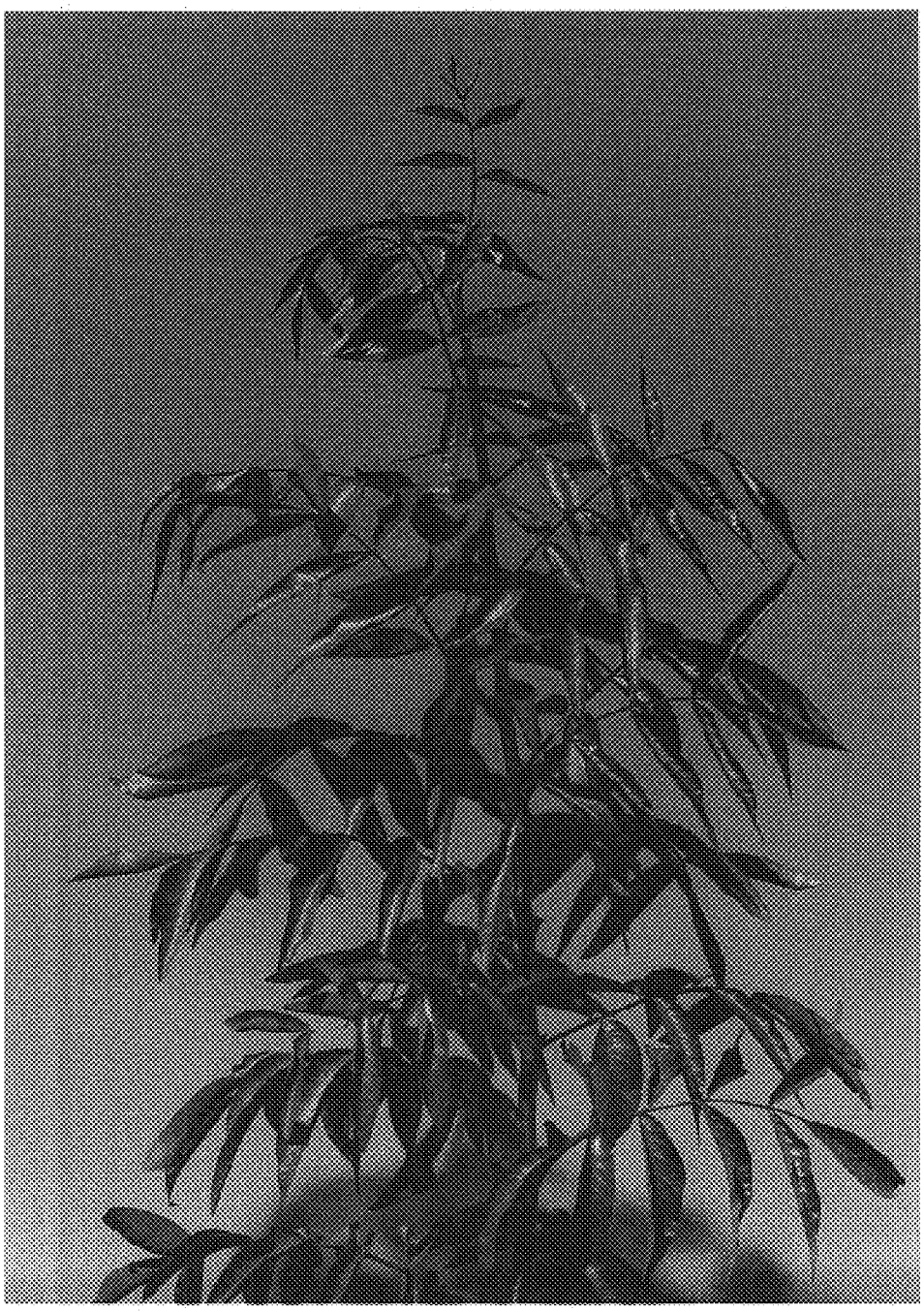
FIG. 3 shows a close-up of the new variety with both medium red to reddish green new leaflets and dark green older leaflets.

*Leaflets.*—Small, with young tissue glossy and lighter green than older tissue, which is dull and darker green. Shape: Medium length and lanceolate, apex acute, base acute but less so than apex. Color: New leaflets are medium red to a reddish green, near Greyed-red Group 173A, as shown in FIG. 3. Older leaflets are dark green, near Greyed-green Group 191A, also as shown in FIG. 3. Arrangement: pinnately compound of eleven, sometimes less, nearly opposite, lanceolate and sessile. Margin, venation pattern and color, length (without petiole), width, and texture: Entire with a pinnate and alternate venation pattern; veins are light green, near 194D. Apex of leaflets is acute. Base of leaf cuneate. The length of the leaflet averages 2.61 inches and 0.938 inches wide at widest spot. The leaflet has a leathery characteristic on top with a smoother surface on bottom. Leaf surface is glabrous. Leaflet Ribs: The center rib on leaves are deepened. Ribs of leaflets start at the base as deep red (near 178A) and progressively turn green at the tip of the leaflet (near 194D). The veins in leaflets are lighter green than the leaflets.

*Rachis length and color.*—Rachis length is about 4.15 inches; rachis color is greyed-purple, near 183C.

*Petiole length, diameter, and color.*—Petiole length is about 2.11 inches, with a diameter of about 0.076 inches; petiole color is greyed-purple, near 183C.

Growth:

*Trunk.*—Trunk is rounded.

*Trunk color.*—The trunk is light brown in color, near Greyed-orange Group 174B, on older growth and red, near Greyed-red Group 178A, in newer growth.

*Trunk diameter.*—About 1.64 inches at 12.3 inches above soil surface.

*Bark texture.*—Rough.

*Vegetative buds.*—Vegetative buds are small and reddish on new growth and green and larger on older growth.

We claim:

1. A new and distinct variety of pistachio tree, identified as 'P.N. 1-15', substantially as shown and described.

* * * * *